United States Patent [19]

Anderson

[11] Patent Number: 5,072,625
[45] Date of Patent: Dec. 17, 1991

[54] LIQUID LEVEL AND SAMPLING GAUGE

[76] Inventor: Robert V. Anderson, 4617 Ranch View Rd., Fort Worth, Tex. 76109

[21] Appl. No.: 514,191

[22] Filed: Apr. 25, 1990

[51] Int. Cl.$^5$ .......................... G01N 1/12; G01F 23/04
[52] U.S. Cl. ................................ 73/864.63; 73/863.86; 33/717; 33/723
[58] Field of Search ............ 73/864.63, 864.66, 864.65, 73/824.67, 863.86; 33/717, 718, 723

[56] References Cited

U.S. PATENT DOCUMENTS

| | | | |
|---|---|---|---|
| 397,961 | 2/1889 | Bergmann | 73/864.63 |
| 1,150,600 | 8/1915 | Jay, Jr. | 33/723 |
| 2,213,026 | 8/1940 | Hoffman | 33/723 |
| 2,544,262 | 3/1951 | Hall | 33/717 |
| 2,580,711 | 1/1952 | Weidinger | 73/864.65 |
| 3,169,322 | 2/1965 | Milo | 33/717 |
| 3,371,538 | 3/1968 | Bagby | 33/717 |
| 3,390,463 | 7/1968 | Hirsch | 73/864.65 X |
| 3,438,263 | 4/1969 | Cohen et al. | 73/863.86 |
| 4,292,739 | 10/1981 | Dobbins | 73/864.63 X |
| 4,346,519 | 8/1982 | Milo | 73/864.63 X |
| 4,372,382 | 2/1983 | Rooney et al. | 73/864.63 X |
| 4,583,293 | 4/1986 | Smith | 73/864.63 X |
| 4,760,747 | 8/1988 | Fackler | 73/864.65 |

FOREIGN PATENT DOCUMENTS

| | | | |
|---|---|---|---|
| 335407 | 1/1904 | France | 33/717 |
| 568527 | 3/1924 | France | 33/717 |
| 1040538 | 10/1953 | France | 33/717 |
| 257850 | 11/1969 | U.S.S.R. | 73/864.64 |
| 580478 | 11/1977 | U.S.S.R. | 73/864.63 |

*Primary Examiner*—Tom Noland
*Attorney, Agent, or Firm*—Charles D. Gunter, Jr.

[57] ABSTRACT

A liquid level and sampling gauge is shown which includes a stick having a vertical face with a groove formed therein. A transparent sample tube is mounted in the groove and has a bottom opening. A rigid rod is located within the sample tube and has a lower end and an upper end. A valve member is carried on the rod lower end and includes an O-ring which contacts a valve seat provided in the stick lower end when the valve member is moved between an open position which admits liquid to the sample tube and a closed position. A valve operator at the stick upper end moves the valve member between the open and closed positions.

11 Claims, 3 Drawing Sheets

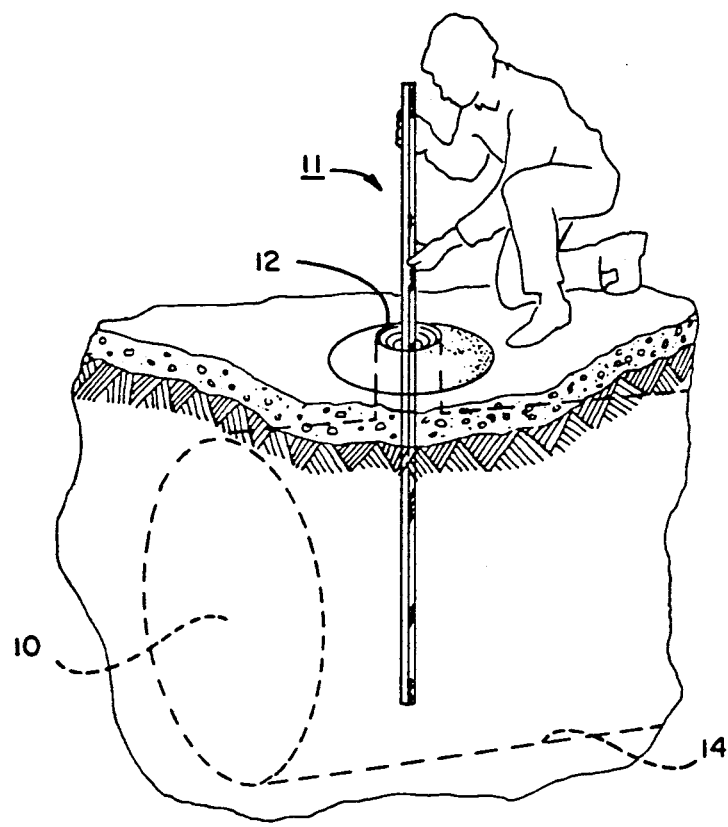
FIG. 1
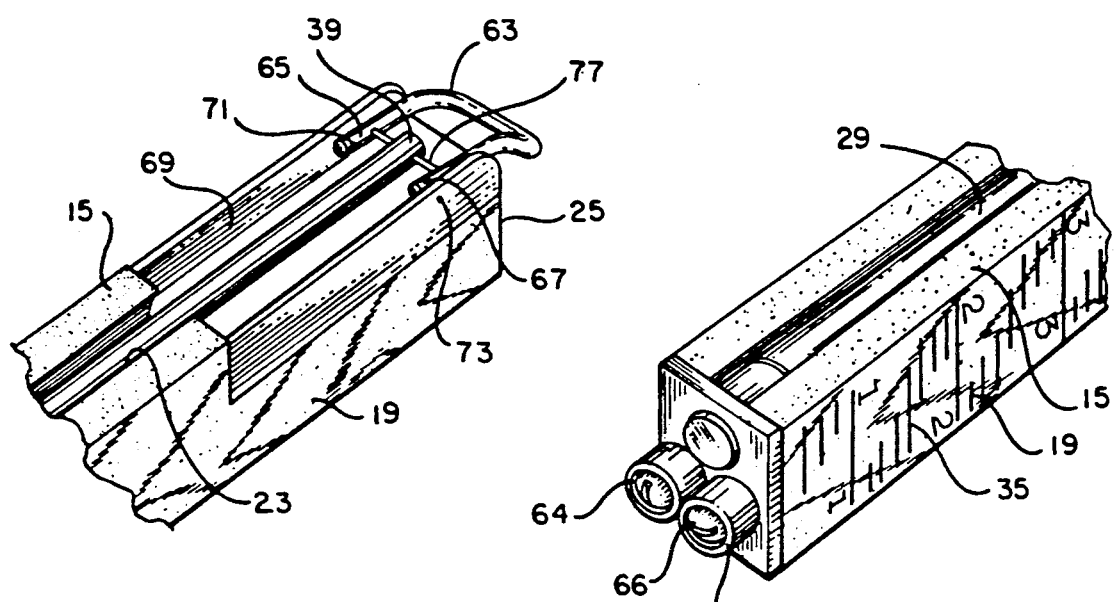
FIG. 2
FIG. 3

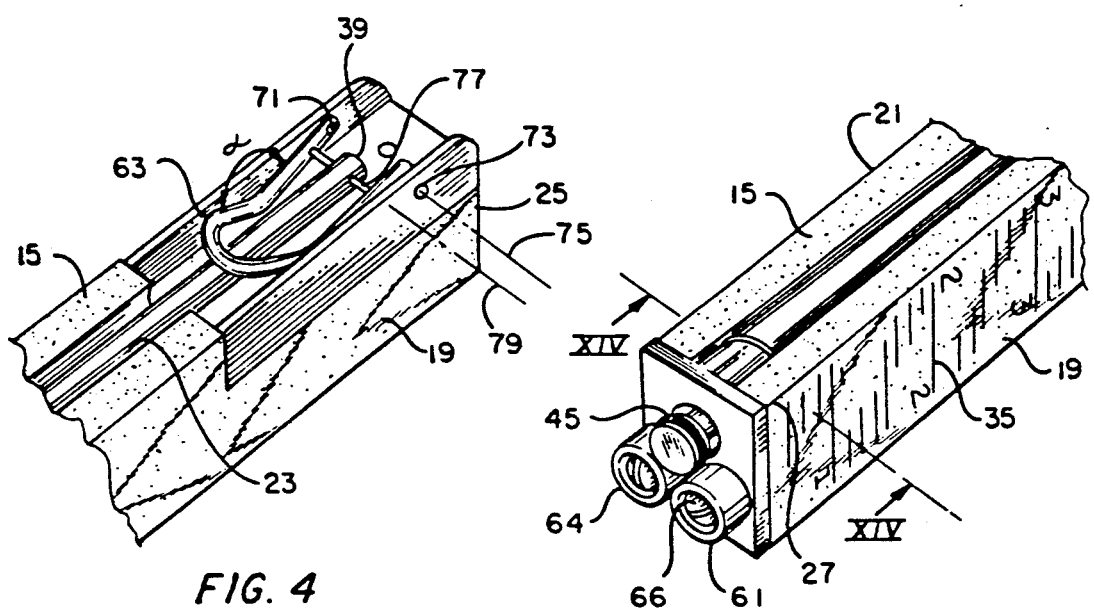
FIG. 4    FIG. 5
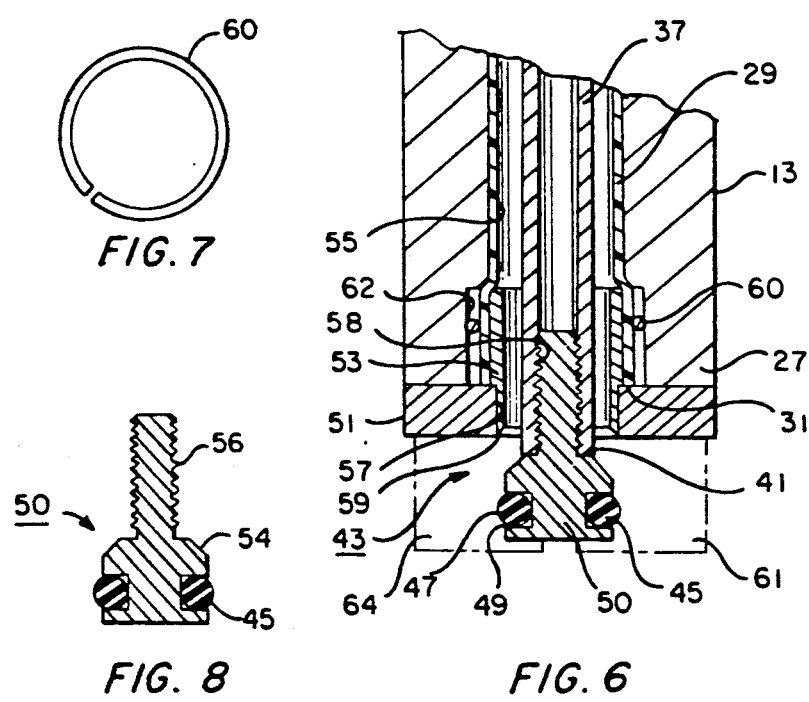
FIG. 7    FIG. 6
FIG. 8

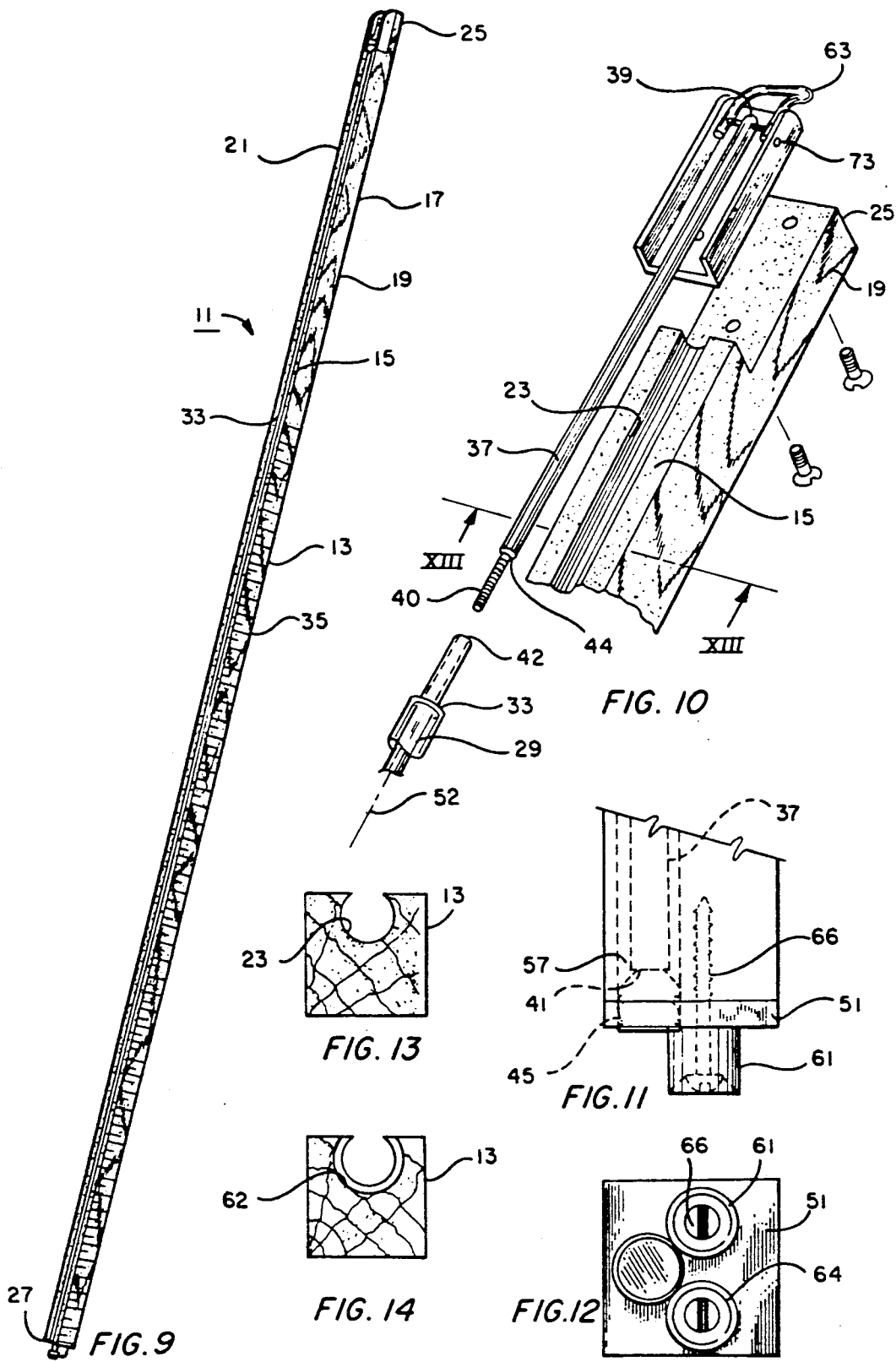

LIQUID LEVEL AND SAMPLING GAUGE

BACKGROUND OF THE INVENTION

1. Field of the Invention

This invention relates generally to the field of gauge and tank sampler devices and, specifically, to a dip stick for measuring the amount of liquid in a deep container such as an underground petroleum storage tank.

2. Description of the Prior Art

A variety of liquid level indicators are known in the prior art. One of the simplest is the dip-stick, which is an elongate member typically formed from wood or metal which can be inserted into an underground tank and then withdrawn, the liquid level in the tank being determined by observing the height to which the liquid has wetted the dip-stick. The wetted height on the stick is compared with a suitable calibration. The calibration could be, for instance, in the form of an external chart or in the form of graduations imprinted on the dip-stick itself.

Although the traditional dip-stick is a simple and economical means of estimating liquid levels, it suffers from several disadvantages. Although it is capable of measuring the level of liquid in the tank, it ordinarily cannot distinguish between one liquid and another (for example water and gasoline). It gives no indication of the character of the liquid, such as whether the liquid is clean or dirty.

Another disadvantage of the simple dip-stick is the lack of precision in the level reading which is obtained. Conventional dip-sticks generally rely upon the surface attraction between the material of the stick and the liquid to provide an observable, wetted surface level indication on the face of the stick. In order to provide a more precise reading, the stick may be powdered in an attempt to better delineate the liquid level. However, wave action in the tank or capillary action of the liquid contacting the powder can cause inaccuracies in the reading.

Accordingly, the present invention has as its object to provide a simple and convenient way to more accurately measure the liquid level of liquid in a container, such as an underground liquid storage tank.

Another object of the invention is to provide a device and method for measuring liquid level in an underground liquid storage tank which does not rely upon the low surface attraction between the exterior of the stick and the liquid in the tank.

Another object of the invention is to provide a level indicating device which also allows sampling of the liquid in the tank to provide an indication of the character of the liquid and which is capable of distinguishing between one liquid and another.

SUMMARY OF THE INVENTION

The liquid level and sampling gauge of the invention comprises an elongate stick having an elongate, vertical face with groove formed therein. A transparent sample tube is mounted in the groove and extends at least partly up the elongate, vertical face of the stick. The sample tube has a bottom opening and a top opening. A rigid rod is located within the sample tube and has an upper end and a lower end which normally extends at least partly from the sample tube bottom opening. A valve means is located on the rod lower end and is moveable between an open and closed positions to alternately allow liquid to pass into the sample tube when in the open position and to prevent passage of liquid when in the closed position. A valve operator is connected to the rod upper end for moving the valve means between the open and closed positions.

Preferably, the valve means comprises an O-ring carried in an O-ring groove provided on the rod lower end. The O-ring is adapted to slidingly engage a valve seat provided adjacent the tube bottom opening as the rod is moved vertically upward within the tube.

The valve operator preferably comprises an over-center mechanism for alternately shifting the rod within the tube in upward and downward vertical directions, whereby the valve means is shifted between the closed and open positions, respectively.

A selected face of the elongate stick is preferably calibrated with graduations representative of the liquid level within the tank. Since the valve means displaces a known volume of liquid within the sample tube when the valve means is moved from the open to the closed positions, the graduations on the face of the stick are offset by an amount equal to the known volume displacement within the sample tube caused by the closing of the valve means.

Additional objects, features and advantages will be apparent in the written description which follows.

BRIEF DESCRIPTION OF THE DRAWINGS

FIG. 1 shows an underground storage tank in dotted lines with the liquid level and sampling gauge being lowered into the top opening of the tank;

FIG. 2 is an enlarged view of the top end of the gauge of FIG. 1 showing the over-center mechanism in the fully closed position;

FIG. 3 is an enlarged view of the bottom end of the gauge showing the valve means in the closed position;

FIG. 4 is a view similar to FIG. 2 showing the over-center mechanism in the fully open position;

FIG. 5 is a view similar to FIG. 3 showing the valve means in the open position;

FIG. 6 is an enlarged, cross-sectional view of the lower end of the gauge of FIG. 1 showing the valve means and valve seat in greater detail;

FIG. 7 is an isolated view of the retaining ring used in the lower end of the gauge;

FIG. 8 is an isolated view of the valve means;

FIG. 9 is a perspective view of the front and left sides of the liquid level and sampling gauge of the invention;

FIG. 10 is an exploded view of the gauge upper end showing the over-center mechanism and rigid rod;

FIG. 11 is a side view of the gauge lower end showing the valve means in dotted lines and in the closed position within the valve seat;

FIG. 12 is a bottom view of the gauge of the invention;

FIG. 13 is a cross-sectional view taken along lines XIII.—XIII. in FIG. 10; and

FIG. 14 is a cross-sectional view taken along lines XIV.—XIV. in FIG. 5.

DETAILED DESCRIPTION OF THE INVENTION

FIG. 1 shows a liquid level and sampling gauge of the invention designated generally as 11. The gauge 11 is particularly adapted for sampling the liquid contents of a tank 10 (shown in dotted lines) having a tank top opening 12 and a tank bottom 14 such as the underground tank used for storing flammable or corrosive liquids. For instance, the gauge 11 is well adapted for use in measuring the level of gasoline or diesel fuel in an underground petroleum storage tank.

The gauge 11 includes an elongate, calibrated support member, such as stick 13 (FIG. 9), of sufficient length to extend from the tank top opening 12 to the tank bottom 14 to measure liquid levels within the tank. The stick 13 has an elongate, front vertical face 15 (FIGS. 1 and 5), a rear vertical face 17 and left and right faces 19, 21, respectively. The elongate vertical face 15 is provided with a longitudinal groove 23 which runs from the upper end 25 to the lower end 27 of the stick 13. As shown in FIGS. 13 and 14, the bore of the groove 23 is stepped to form an enlarged opening adjacent the stick lower end 27.

As shown in FIGS. 3 and 6, a transparent sample tube 29 formed from a flexible, synthetic elastomer formulated for continuous immersion in hydrocarbon fuels is mounted in the groove 23 and extends at least partly up the elongate vertical face 15 of the stick 13. The sample tube 29 has a bottom opening 31 and a top opening 33 (FIG. 6 and 10). As shown in FIGS. 3, 5 and 9, the stick 13 is calibrated by means of graduations 35 provided on the left face 19 of the stick adjacent the transparent sample tube 29 and running for substantially the length of the sample tube 29. The graduations 35 could be, for example, in inches to represent the height of liquid caught in the sample tube, as will be explained. The graduations could then either be compared to a calibration chart to convert the measured liquid height to a volume of liquid in the tank or, the graduations could themselves represent a conversion of the measured liquid level to liquid volume in the tank.

A hollow, rigid rod 37 (FIGS. 6 and 10) is located within the sample tube 29 and has an upper end 39 and a lower end 41 which normally extends at least partly from the sample tube bottom opening 31. The hollow, rigid rod 37 also has a threaded connection at one point along its length. This connection can be formed, for example, by a threaded stud 40 which is received within mating threaded bores provided in the ends 42, 44 of the hollow rod. As will be explained, the threaded connection allows threaded adjustment of the length of the rigid rod 37 to compensate for changes in the dimensions of the stick 13 due to moisture, temperature, and the like.

Valve means, designated generally as 43 in FIG. 6, are located on the rod lower end 41 and are moveable between an open position shown in FIG. 6 and a closed position shown in FIGS. 3 and 11 to alternately allow liquid to pass into the sample tube 29 when in the open position and to prevent passage of liquid out of the sample tube when in the closed position. As best seen in FIG. 6, the valve means preferably comprises an O-ring 45 carried between an upper flange 47 and a lower flange 49 of a valve element 50 secured to the rod lower end 41. The O-ring 45 rests in a groove defined between the upper and lower flanges 47, 49 and lies in a plane generally perpendicular to the longitudinal axis 52 (FIG. 10) of the rod 37.

The valve element 50 (FIG. 8) has a frustoconical region 54 above the O-ring groove which serves to guide the valve element 50 and the associated lower end 41 of the rigid rod within the opening provided in the stick lower end. The valve element 50 is secured to the rod lower end 41 by means of an externally threaded extent 56 received within a mating bore 58 in the rod lower end. A sealant or glue can be applied to the threaded connection to avoid leak of the sample into the rod 37 when the sample is captured.

As shown in FIG. 6, the stick is provided with a rigid sole plate 51, preferably formed of metal or rigid plastic, which covers the lower end 27 thereof, the sole plate 51 having an upwardly extending rigid sleeve 53 integral therewith which is received concentrically within the bottom opening 31 of the tube and extending at least partly within the interior thereof so that the O-ring 45 engages the interior 57 of the sleeve 53 rather than the interior 55 of the sample tube 29. The rigid sleeve 53 is also preferably provided with a radiused, i.e., chamfered mouth opening 59 which forms a valve seat for the valve means when the valve means is moved to the closed position. As seen in FIG. 6, the resilient sample tube 29 deforms slightly and bells out around the exterior of the rigid sleeve 53 when the sleeve 53 is installed into position. Retaining means, such as split wire ring 60 are engaged about the exterior of the tube 29 once the rigid sleeve 53 is received within the interior of the tube 29 to thereby seal the tube about the exterior of the rigid sleeve 53. The split wire ring 60 fits snugly within the larger diameter provided by the counterbore 62 provided at the stick lower end.

The stick lower end 27 can also be provided with one or more bumpers 61, 64 on the sole plate 51 which extend vertically past the valve means to prevent damage to the valve means when the stick contacts the tank bottom. Bumpers 61, 64 are resilient members secured by wood screws 66 to the stick bottom. The bumpers 61, 64 also assist in guiding the rod lower end 41 and valve means 43 during their path of travel.

A valve operator such as bail 63 is connected to the rod upper end 39 for moving the valve means 43 between the open and closed positions. Preferably, the valve operator comprises an over-center mechanism for alternately shifting the rod 37 within the sample tube 29 in upward and downward vertical directions, whereby the valve means 43 is shifted between the closed and open positions shown in FIGS. 3 and 5, respectively. The preferred over-center mechanism comprises a U-shaped bail 63 having a pair of spaced-apart ends 65, 67, each of the spaced-apart ends 65, 67 (FIG. 2) being pivotally mounted within a channel-like opening 69 provided at the upper end 25 of the stick 13.

Each of the spaced-apart ends 65, 67 is pivotally mounted by means of horizontal pins 71, 73 for movement about a first pivot axis (designated as 75 in FIG. 4.) The rod upper end 39 is pivotally connected to the bail spaced-apart ends 65, 67 by a longitudinal pin 77 to define a second pivot axis 79. Movement of the second pivot axis 79 in an arcuate path about the first pivot axis 75 causes alternate shifting of the rod 37 within the sample tube 29. The bail 63 thus acts as an over-center mechanism to secure the valve means 43 in the open and closed positions. The bail outer extent is bent at an angle $\alpha$ (FIG. 4) in order to facilitate grasping the bail when moving the bail from the open position to the closed position.

As the valve means 43 moves from the open position shown in FIGS. 5 and 6 to the closed position shown in FIG. 3, it can be seen that the valve means 43 moves at least partly within the interior 57 of the rigid sleeve 53. Thus, the valve means 43 displaces the entire contents of the sample tube 29 upwardly by a constant distance, which distance represents a known volume of liquid within the sample tube. In order to compensate for this displacement, the graduations 35 on the face 19 of the stick 13 are offset by an amount equal to the known volume displacement within the sample tube caused by the closing of the valve means 43. In this way, the observed, wetted surface level within the sample tube 29 and calibrated level can be offset purposefully to compensate for the closing of the valve means and provide a true indication of the level of liquid.

The operation of the gauge will now be briefly described. In order to measure the liquid level within a tank, the bail 63 of the over-center mechanism is moved to the position shown in FIG. 4 so that the valve means 43 is opened. This action locks the valve element 50 in the open position approximately ¼" below the valve seat to permit free entry of liquids into the gauge tube 29. The stick is then inserted through the top opening of the tank and lowered until the bumper 61 contacts the tank bottom. As the stick is being lowered within the tank, liquid within the tank enters the mouth opening 59 and passes upwardly within the sample tube 29. After about 5 seconds or less, the liquid which has entered the tube will stabilize. Once the liquid within the sample tube has reached its own level, the bail 63 is shifted to the closed position shown in FIG. 2 so that the mouth opening 59 is closed by the valve means 43. The liquid level can be determined by withdrawing the gauge from the tank 10 and comparing the liquid level within the sample tube 29 with the graduations 35 on the stick vertical face. Because the sample tube 29 provides a visual indication of the nature of the liquid of liquids, the observer can determine if more than one liquid is present and whether the liquid is clear or dirty.

An invention has been provided with several advantages. The liquid level sampling stick of the invention is simple in design and economical to manufacture. The liquid level of a petroleum storage tank can be easily determined for product inventory purposes. The water content of the tank, as well as other liquid content, can be determined by subtracting the height of the water column from the total liquid volume measured on the stick and converting to, for example, gallons if this is the unit of measure being used. The O-ring valve means provides a simple and efficient mechanism for opening and closing the mouth opening to the sample tube. The device does not employ spring biasing means or other complicated valving mechanisms. The over-center mechanism provides a convenient and simple means for shifting the valve and locking the mechanism in either the open or closed positions.

Because the valve means is pulled upwardly within the mouth opening to the sample chamber, and because the valve means displaces a known volume of liquid, the stick graduations can be offset by a known, constant amount to provide an accurate indication of the liquid level being measured. This provides an accurate check that the sample captured is correct, since the wet-line on the exterior of the stick and the sample level within the tube are always displaced by, for instance, ¼". If the wet-line/sample level offset is greater than ¼", the sample has been incorrectly taken and should be repeated.

The stick, sample tube, rod and valve means can all be formed from non-conductive materials.

While the invention has been shown in only one of its forms, it is not thus limited but is susceptible to various changes and modifications without departing from the spirit thereof.

I claim:

1. A liquid level and sampling gauge, comprising:

an elongate stick having an elongate, vertical face with a groove formed therein;

a transparent sample tube mounted in said groove and extending at least partly up said elongate, vertical face of said stick, said sample tube having a bottom opening and a top opening;

a rigid rod located within said sample tube and having an upper end and a lower end which normally extends at least partly from said sample tube bottom opening;

valve means located on said rod lower end, said valve means being movable between open and closed positions to alternately allow liquid to pass therethrough when in the open position and to prevent passage of liquid when in the closed position;

a valve operator connected to the rod upper end for moving the valve means between the open and closed positions;

wherein said valve means comprises an O-ring carried in an O-ring groove provided on said rod lower end, said O-ring being adapted to slidingly engage a valve seat provided adjacent said tube bottom opening as said rod is moved vertically upward within said tube; and wherein said tube is formed of a flexible synthetic elastomer and wherein said stick is provided with a rigid sole plate, said sole plate including an upwardly extending rigid sleeve which is received concentrically within the interior of said tube so that the O-ring engages the interior of the sleeve rather than the interior of the tube.

2. The liquid level and sampling gauge of claim 1, wherein said valve operator comprises an over-center mechanism for alternately shifting said rod within said tube in upward and downward vertical directions, whereby said valve means is shifted between the closed and open positions, respectively.

3. The liquid level and sampling gauge of claim 2, wherein said over-center mechanism comprises a U-shaped bail having a pair of spaced apart ends, each of said spaced-apart ends being pivotally mounted within a channel like opening provided at the end of said stick opposite said valve means for pivotal movement about a first pivot axis, and wherein said rod upper end is pivotally connected to said bail between said ends thereof at a second pivot axis, whereby movement of the second pivot axis in an arcuate path about the first pivot axis causes alternate shifting of the rod within the tube.

4. A liquid level and sampling gauge for sampling the liquid contents of a tank of the type having a tank top tank opening and a tank bottom, the liquid level and sampling gauge, comprising:

an elongate, calibrated stick of sufficient length to extend from said tank bottom through said tank top opening to measure liquid levels within said tank, said stick having an elongated vertical face with a groove formed therein;

a transparent sample tube mounted in said groove and extending at least partly up said elongate, vertical face of said stick, said sample tube having a bottom opening and a top opening, and wherein said stick is calibrated by means of graduations provided on said stick adjacent said transparent sample tube;

a rigid rod located within said sample tube and having an upper end and a lower end which normally extends at least partly from said sample tube bottom opening;

valve means located on said rod lower end, said valve means being movable between open and closed positions to alternately allow liquid to pass therethrough when in the open position and to prevent passage of liquid when in the closed position;

a valve operator connected to the rod upper end for moving the valve means between the open and closed positions;

wherein said valve means comprises an o-ring carried in an o-ring groove provided on said rod lower end, said o-ring being adapted to slidingly engage a valve seat provided adjacent said tube bottom opening as said valve means is moved between the open and closed positions;

wherein said valve means displaces a known volume of liquid within said sample tube when said valve means is moved from the open to the closed positions, and wherein said graduations on said stick is offset by an amount equal to the known volume displacement within the sample tube caused by the closing of the valve means;

wherein said valve operator comprises an over-center mechanism for alternately shifting said rod within said tube in upward and downward vertical directions, whereby said valve means is shifted between the closed and open positions, respectively; and wherein said over-center mechanism comprises a U-shaped bail having a pair of spaced apart ends, each of said spaced-apart ends being pivotally mounted within a channel like opening provided at the end of said stick opposite said valve means for pivotal movement about a first pivot axis, and wherein said rod upper end is pivotally connected to said bail between said ends thereof at a second pivot axis, whereby movement of the second pivot axis in an arcuate path about the first pivot axis causes alternate shifting of the rod within the tube.

5. The liquid level and sampling gauge of claim 4, wherein said rigid rod includes a threaded connection at one point along its length, said threaded connection allowing screw threaded adjustment of the length of the rigid rod, to compensate for changes in the dimensions of the elongate calibrated stick.

6. The liquid level and sampling gauge of claim 5, wherein said tube is formed of a flexible synthetic elastomer and wherein said stick is provided with a rigid sole plate, said sole plate including an upwardly extending rigid sleeve which is received concentrically within the interior of said tube so that the o-ring engages the interior of the sleeve rather than the interior of the tube.

7. The liquid level and sampling gauge of claim 6, wherein retaining means are engaged about the exterior of the tube once the rigid sleeve is received within the interior of the tube to thereby seal the tube about the exterior of the rigid sleeve.

8. The liquid level and sampling gauge of claim 7, wherein the retaining means is a split wire ring.

9. The liquid level and sampling gauge of claim 8, wherein the rigid sleeve is provided with a chamfered opening which serves as the valve seat for the valve means.

10. The liquid level and sampling gauge of claim 9, wherein the lower end of said rigid rod includes a frustoconical region above said o-ring groove which serves to guide said lower end within said chamfered opening.

11. The liquid level and sampling gauge of claim 10, wherein at least one bumper is provided on the sole plate and extends vertically past the valve means to prevent damage to the valve means when the stick contacts the tank bottom.

* * * * *